United States Patent
Jadhav et al.

(10) Patent No.: US 12,178,996 B2
(45) Date of Patent: Dec. 31, 2024

(54) PRESSURE ACTUATED UNI-DIRECTIONAL FLOW CONTROL DEVICE FOR GRAVITY IV SETS

(71) Applicant: CareFusion 303, Inc., San Diego, CA (US)

(72) Inventors: Amarsinh Deeliprao Jadhav, Bangalore (IN); Rakesh Thulasiram, Bengaluru (IN); Suhas Hanumantharao, Bengaluru (IN); Roy Raju, Malappuram (IN); Sriram Rajaraman, Kumbakonam (IN); Sabarinathan Rajendran, Krishnagiri (IN)

(73) Assignee: CareFusion 303, Inc., San Diego, CA (US)

( * ) Notice: Subject to any disclaimer, the term of this patent is extended or adjusted under 35 U.S.C. 154(b) by 251 days.

(21) Appl. No.: 17/406,674

(22) Filed: Aug. 19, 2021

(65) Prior Publication Data
US 2022/0088300 A1    Mar. 24, 2022

Related U.S. Application Data

(60) Provisional application No. 63/080,567, filed on Sep. 18, 2020.

(51) Int. Cl.
*A61M 5/168* (2006.01)
*A61M 5/38* (2006.01)
(Continued)

(52) U.S. Cl.
CPC .... *A61M 5/16831* (2013.01); *A61M 5/16881* (2013.01); *A61M 5/38* (2013.01);
(Continued)

(58) Field of Classification Search
CPC ...... A61M 5/16827; A61M 2039/2473; A61M 39/227; A61M 5/16831; A61M 5/16881;
(Continued)

(56) References Cited

U.S. PATENT DOCUMENTS 702,195 A * 6/1902 Furman ................ F16K 17/00
                                                  137/466
1,010,834 A * 12/1911 Westburg ............. F16K 17/00
                                                  137/505.47
(Continued)

FOREIGN PATENT DOCUMENTS

WO    WO-2018075390 A1    4/2018

OTHER PUBLICATIONS

Paul Seeburger, 6.6: Moments and centers of mass, Libretexts, MTH 211 Calculus II, p. 1 (Year: 2023).*

(Continued)

*Primary Examiner* — Jason E Flick
*Assistant Examiner* — Adam J. Cermak
(74) *Attorney, Agent, or Firm* — Morgan, Lewis & Bockius LLP (57) ABSTRACT

A flow control device includes a housing having a primary inlet, a secondary inlet, and an outlet disposed downstream of the primary and secondary inlets. The flow control device further includes a chamber defined by an inner circumferential surface of the housing. The chamber fluidly connects the primary and secondary inlets with the outlet. A valve member is mounted in the chamber to pivot toward and block the primary inlet by fluid pressure in the secondary inlet when fluid pressure into the secondary inlet is higher than fluid pressure into the primary inlet.

17 Claims, 2 Drawing Sheets

(51) Int. Cl.
*F16K 11/052* (2006.01)
*F16K 15/03* (2006.01)

(52) U.S. Cl.
CPC .. *A61M 2005/16868* (2013.01); *F16K 11/052* (2013.01); *F16K 15/038* (2013.01)

(58) Field of Classification Search
CPC ........ A61M 2005/1406; A61M 5/1411; A61M 5/1689; A61M 5/1408; A61M 39/22; A61M 5/38; A61M 2039/266; Y10T 137/2607; Y10T 137/2564; Y10T 137/2567; F16K 17/02; F16K 15/03; F16K 15/14; F16K 15/144; F16K 15/147; F16K 15/148; F16K 15/16; F16K 15/1401; F16K 15/1402; F16K 15/1481; F16K 15/035; F16K 15/036; F16K 15/038
See application file for complete search history.

(56) References Cited

U.S. PATENT DOCUMENTS

| | | | | |
|---|---|---|---|---|
| 3,202,165 | A * | 8/1965 | Yavicoli | E03F 7/04 137/107 |
| 3,586,038 | A * | 6/1971 | Jahrstorfer | F16K 15/035 137/527.4 |
| 3,610,698 | A * | 10/1971 | Gachot | F16K 11/02 137/856 |
| 3,705,602 | A * | 12/1972 | Nordin | F16K 11/052 137/527.4 |
| 3,974,848 | A * | 8/1976 | Wheatley | F16K 11/052 137/527 |
| 4,005,726 | A * | 2/1977 | Fowler | F16K 31/002 335/146 |
| 5,732,737 | A * | 3/1998 | Condon | F16K 15/035 137/563 |
| 5,941,270 | A * | 8/1999 | Nogle | F16K 11/052 137/112 |
| 6,186,175 | B1 * | 2/2001 | Frisch | F16K 11/0525 137/625.66 |
| 6,484,754 | B1 * | 11/2002 | Muth | F16K 11/052 137/625.66 |
| 7,322,376 | B2 * | 1/2008 | Frisch | F16K 31/006 137/625.5 |
| 9,309,656 | B2 * | 4/2016 | Burd | F16K 17/12 |
| 2002/0029021 | A1 * | 3/2002 | Bormann | A61M 5/1411 604/252 |
| 2003/0212381 | A1 * | 11/2003 | Whitehead, III | A61M 5/16827 604/514 |
| 2017/0120035 | A1 * | 5/2017 | Butterfield | A61M 5/1409 |
| 2020/0025308 | A1 * | 1/2020 | Carmody | A61B 6/032 |
| 2020/0038584 | A1 * | 2/2020 | Butterfield | A61M 5/142 |
| 2020/0362546 | A1 * | 11/2020 | Lei | F16K 15/04 |
| 2023/0046809 | A1 * | 2/2023 | Plachetka | F16K 31/52 |

OTHER PUBLICATIONS

International Search Report and Written Opinion for Application No. PCT/US2021/050739, dated Jan. 5, 2022, 13 pages.

* cited by examiner

PRESSURE ACTUATED UNI-DIRECTIONAL FLOW CONTROL DEVICE FOR GRAVITY IV SETS

CROSS-REFERENCES TO RELATED APPLICATIONS

This application claims the benefit of priority under 35 U.S.C. § 119 to U.S. Provisional Patent Application Ser. No. 63/080,567 entitled "PRESSURE ACTUATED UNI-DIRECTIONAL FLOW CONTROL DEVICE FOR GRAVITY IV SETS" filed on Sep. 18, 2020, the disclosure of which is hereby incorporated by reference in its entirety for all purposes.

TECHNICAL FIELD

The present disclosure generally relates to flow control devices, and more particularly to flow control devices having a valve member capable of preventing under-infusion in IV sets with a secondary line, as well as preventing backflow of drug from the secondary line into the primary line.

BACKGROUND

Infusion IV sets are generally used in infusion therapy in order to deliver medication from a pre-filled container, e.g., an IV bottle or bag containing the desired medication, to a patient. Generally, the IV tubing is connected to a catheter and inserted into the localized area to be treated. In some cases, there is a need to deliver multiple medications to the patient in potentially differing dosages, thereby causing the need for an IV extension set having multiple branches of tubings or fluid lines through which the multiple medications may be dispensed to the patient.

Patients are commonly injected with IV solutions that are initially provided in the IV bottle or bag and dripped into the vein of the patient through an IV line. A flow control device, for example, a check valve, is also commonly included in the IV line to permit fluid flow only in the direction of the patient. This ensures that the medication flows downstream toward the patient, not upstream toward the IV bottle or bag.

During infusion with IV sets, a secondary drug feed could potentially flow backwards into primary IV line leading to under infusion of the secondary drug. Though a check valve may be positioned in the primary line to prevent backflow, check valves are prone to frequent failure. A common reason for check valve failure is due to debris existing in infusates. Additionally, under-infusion frequently occurs due to air entering the secondary line thereby causing some of the secondary drug to remain in the secondary line (undelivered medication). Air entering the IV line may have undesirable effects such as causing air embolisms for the patient.

The description provided in the background section should not be assumed to be prior art merely because it is mentioned in or associated with the background section. The background section may include information that describes one or more aspects of the subject technology.

SUMMARY

According to various embodiments of the present disclosure, a flow control device may include a housing having a primary inlet, a secondary inlet, and an outlet disposed downstream of the primary and secondary inlets. A chamber may be defined by an inner circumferential surface of the housing. The chamber may fluidly connect the primary and secondary inlets with the outlet. The flow control device may further include a valve member mounted in the chamber to pivot toward and block the primary inlet by fluid pressure in the secondary inlet when fluid pressure into the secondary inlet is higher than fluid pressure into the primary inlet.

According to various embodiments of the present disclosure, a flow control device may include a housing having an inner circumferential surface defining a chamber. The housing may include a primary inlet configured to receive a primary fluid line, a secondary inlet configured to receive a secondary fluid line, and an outlet disposed downstream of the primary and secondary inlets. The flow control device may further include a valve member mounted on the inner circumferential surface. The valve member may include a lever having first and second ends, a fulcrum on which the lever is supported and pivoted, a primary line sealing member disposed at the first end at a position corresponding to the primary inlet, and a secondary line sealing member disposed at the second end at a position corresponding to the secondary inlet.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

The present description relates in general to flow control devices, and more particularly to flow control devices having a valve member capable of preventing under infusion in IV sets with a secondary fluid line, as well as preventing backflow of drug from the secondary fluid line into the primary fluid line.

IV sets with a secondary fluid line tend to experience under infusion of the secondary drug due to failure of the check valve in the primary fluid line. The most frequent causes of failure of the check valve are due to debris accumulated at the time of spiking and seeping of drug in the secondary fluid line into the primary fluid line at low pressures. A common cause of under-infusion is dilution of drug at the time of back priming of the secondary IV and also at the time of equal head in the primary and secondary fluid lines. Other causes include dead volume in the secondary fluid line, as well as time taken to infuse the drug. The flow control devices of the various embodiments described herein overcome the above issues commonly associated with IV sets having primary and secondary fluid lines.

Figure 1:
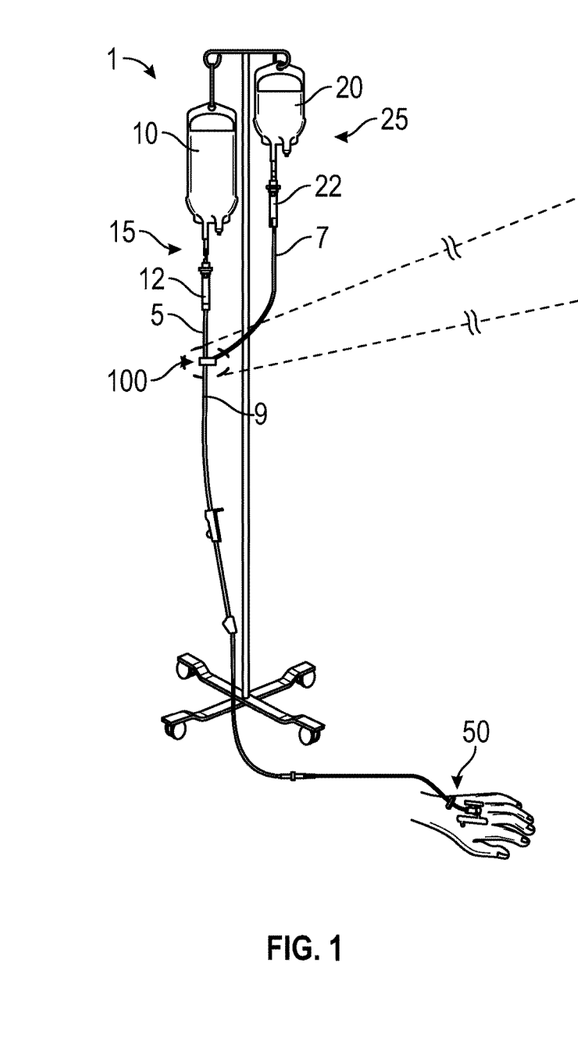
FIG. 1 illustrates an IV extension set that includes a flow control device, in accordance with some embodiments of the present disclosure.

FIG. 1 illustrates a multiple line IV extension set 1 that includes a flow control device 100 in accordance with some embodiments of the present disclosure. As depicted, IV set 1 includes a primary fluid system 15 and a secondary fluid system 25. An IV pump (not shown) receives fluid from primary fluid system 15 and secondary fluid system 25 via a primary IV fluid line 5 and a secondary IV fluid line 7, and may control and dispense the fluids therefrom to a patient 50.

In some embodiments, primary fluid system 15 may include a primary fluid source or container such as a primary intravenous (IV) fluid bag 10, which may include or contain a first medical fluid, e.g., saline solution or other medicinal fluid or drug to be administered to the patient 50. In accordance with some embodiments, a secondary fluid system 25 may include a secondary fluid source or container such as a secondary IV fluid bag 20, which may contain a second medical fluid, e.g., drugs or other secondary fluid to be supplied to the patient 50 for treatment. In some embodiments, the second medical fluid may be different from the first medical fluid. However, the various embodiments of the present disclosure are not limited to the aforementioned configuration. In other embodiments, the first and second fluids may be the same.

According to various embodiments of the present disclosure, as illustrated in FIG. 1, primary IV fluid bag 10, which holds a primary fluid may be positioned at a lower axial position or height that the secondary IV fluid bag 20. For example, the primary IV fluid bag 10 may be hung on a suspension system or hanger and then the secondary IV fluid bag 20 may be hung above the primary IV fluid bag and may be coupled to the secondary fluid line 7, which is connected to the primary fluid line 5 via the flow control device 100.

As depicted, primary IV fluid line 5 carries a primary fluid from a drip chamber 12 to flow control device 100. As shall be described further with respect to the following figures, flow control device 100 may be an external flow control device, which fluidly couples or communicates the primary IV fluid line 5 and the secondary IV fluid line 7 with an outlet fluid line 9 in order to allow fluid flow from primary fluid bag 10 and/or secondary fluid bag 20 to the IV pump (not illustrated) via the outlet 9, while preventing reverse flow (backflow) of fluid from secondary fluid system 25 toward primary fluid bag 10.

Figure 2A:
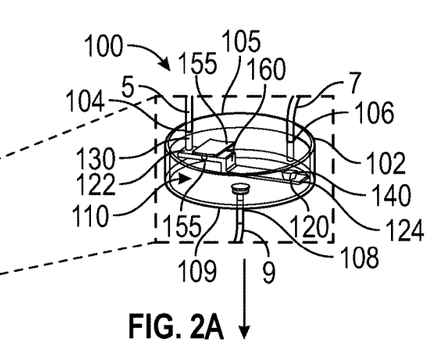
FIG. 2A illustrates a perspective view of the flow control device of FIG. 1, in accordance with some embodiments of the present disclosure.
Figure 2B:
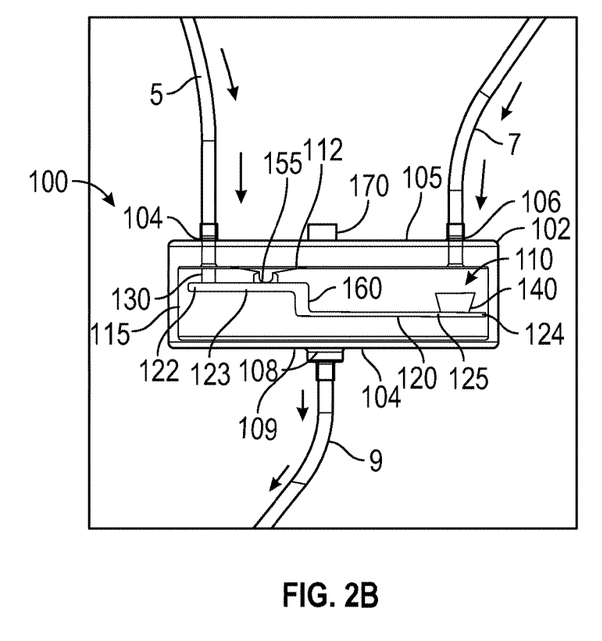
FIG. 2B illustrates an enlarged view of the flow control device and valve member of FIG. 2A, in accordance with some embodiments of the present disclosure.

FIG. 2A is a perspective view of a flow control device, in accordance with some embodiments of the present disclosure. FIG. 2B illustrates an enlarged view of the flow control device and valve member of FIG. 2A, in accordance with some embodiments of the present disclosure. Referring to FIGS. 2A and 2B, the flow control device 100 may have a housing 102 including a primary inlet 104 and a secondary inlet 106. As depicted, the primary inlet 104 and the secondary inlet 106 may be disposed on an upper surface 105 of the housing. The housing 102 may further include an outlet 108 disposed downstream of the primary and secondary inlets 104 and 106. For example, the outlet 100 may be disposed on a lower surface 104 of the housing 102. The outlet 108 may define a fluid path through which medication or drugs (e.g., a first or primary fluid and/or a secondary fluid) from the primary and secondary inlets 104 and 106 may be delivered to the patient 50.

The primary inlet 104 may be configured to receive the primary fluid line 5, and the secondary inlet 106 may be configured to receive the secondary fluid line 7. The outlet 108 may be configured to receive the outlet fluid line 9. The flow control device 100 may further include a chamber 110 defined by an inner circumferential surface 115 of the housing 102. The chamber 110 may include an upper surface 112 fluidly communicated with the primary and secondary inlets 104 and 106 and a lower surface 114 fluidly communicated with the outlet 108. As depicted, the chamber 110 may fluidly connect the primary and secondary inlets 104 and 106 with the outlet 108. Accordingly, the medical fluid from each of the fluid bags 10 and 20 may be may flow from the respective primary and secondary fluid lines 5 and 7 into the chamber 110, and be delivered to the patient 50 via the outlet 9.

According to various aspects of the present disclosure, the flow control device may include a valve member 120 mounted in the chamber 110. The valve member 120 may be pivotally mounted on the upper surface 112 of the chamber 110. In some embodiments, as depicted in FIG. 2B, the valve member 120 may be in the form of a lever having a first end 122 and a second end 124. The lever 125 may have a fulcrum 155 positioned between the first and second ends 122 and 124 of the lever 125. Accordingly, the valve member 120 may be in the form of a Class 1 lever in which the fulcrum is positioned between the load and the effort.

In accordance with various embodiments of the present disclosure, the first and second ends 122 and 124 of the lever 120 may be positioned axially offset from each other. For example, in a non-actuated state of the valve member 120, the first end may be positioned at an axially higher position than the second end 124. As depicted in FIG. 2B, in the non-actuated state, the first end 122 may be positioned upstream of the second end 124. To this effect, the lever 120 may include a transition step 160 disposed between the first and second ends 122 and 124, and having a height corresponding to the axial offset or height between the first and second ends 122 and 124. As illustrated, the lever 120 may include a primary portion 123 and a secondary portion 125. The primary portion 123 may extend from the first end 122 and terminate at the transition step 160. The secondary portion 125 may extend from the transition step 160 and terminate at the second end 124.

In some embodiments, the fulcrum 155 may be positioned on the primary portion 123. Accordingly, the primary portion 123 of lever 120 may be coupled to the upper surface 112 of the chamber 110 to allow the lever 120 to pivot about the fulcrum 155.

According to various embodiments of the present disclosure, the lever 120 may further include a primary line sealing member 130 disposed on the primary portion 123 at a position corresponding to the primary inlet 104. Additionally, the lever 120 may further include a secondary line sealing member 140 disposed on the secondary portion 125 at a position corresponding to the primary inlet 104. For example, in the non-actuated state of the lever 120, the primary line sealing member 130 may be axially aligned with the primary inlet port 140. Similarly, in the non-actuated state of the lever 120, the secondary line sealing member 140 may be axially aligned with the secondary inlet port 106. A distance between the primary line sealing member 130 and the fulcrum 155 may be less than a distance between the secondary line sealing member 140 and the fulcrum 155. Accordingly, as shall be described in further detail below, the valve member or lever 120 may be actuated by fluid pressure in the secondary inlet 106 to pivot toward and block the primary inlet 104 when a secondary medical fluid is being administered from fluid bag 20 and the fluid pressure into the secondary inlet 106 is higher than fluid pressure into the primary inlet 104.

In some embodiments, the flow control device 100 may further include an air vent 170 disposed on an upper surface 105 of the housing 102. The air vent 170 may be fluidly communicated with the chamber 110 for venting out air that is trapped in the secondary medical fluid entering the chamber. Accordingly, the flow control device of the various embodiments described herein is advantageous in that no priming is required of secondary fluid line 7. When the secondary fluid line 7 is fluidly connected to the flow control device 100 with secondary medical fluid flowing into the chamber 110, any air trapped in the secondary medical fluid entering the chamber may be vented out through the air vent 170. In some embodiments, the air vent 170 may have a hydrophilic membrane, which allows air but not liquid to pass through and be vented to the exterior of the flow control device 100.

Figures 3A, 3B, 3C, 3D, 4A, 4B:
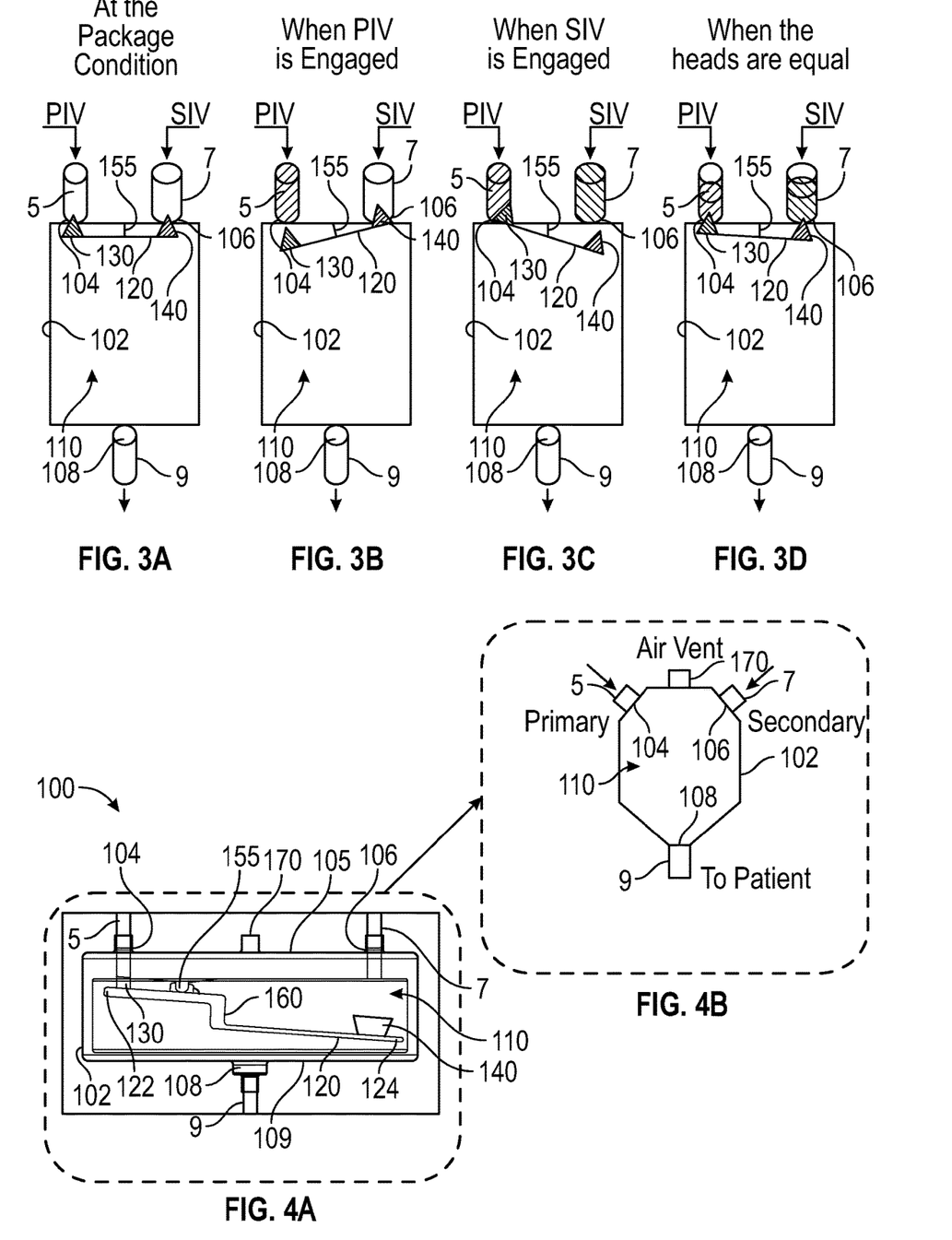
FIG. 3A illustrates a non-actuated operational state of a flow control device and valve member, in accordance with some embodiments of the present disclosure.
FIG. 3B illustrates an operational state of the flow control device and valve member of FIG. 3A where the primary fluid line is engaged and fluid flows only through the primary line, in accordance with some embodiments of the present disclosure.
FIG. 3C illustrates an operational state of the flow control device and valve member of FIG. 3A where both the primary and secondary fluid lines are engaged and fluid pressure in the secondary line is higher than that in the primary fluid line, in accordance with some embodiments of the present disclosure.
FIG. 3D illustrates an operational state of the flow control device and valve member of FIG. 3A when the secondary fluid line has drained to a point where fluid pressure in the primary fluid line equals that in the secondary fluid line, in accordance with some embodiments of the present disclosure.
FIGS. 4A and 4B illustrate a configuration of a flow control device, in accordance with some embodiments of the present disclosure.

FIG. 3A illustrates a non-actuated operational state of a flow control device and valve member, in accordance with some embodiments of the present disclosure. As illustrated, in the non-actuated state of the lever 120, the primary portion 123 of the lever is disposed upstream of the secondary portion 125 of the lever 120. For example, in the non-actuated state of the valve member 120, the primary line sealing member 130 may contact and rest against the upper surface 112 of the chamber 110 while the secondary line sealing member 140 may be axially spaced apart from the upper surface 112 of the chamber 110.

FIG. 3B illustrates an operational state of the flow control device and valve member of FIG. 3A where the primary IV (PIV) fluid line 5 is engaged and fluid flows only through the primary fluid line 5, in accordance with some embodiments of the present disclosure. As depicted, the primary fluid line 5 is attached, fluidly connected to the fulcrum chamber, and then primed as with currently existing IV sets. Due to fluid flowing through the primary fluid line 5, fluid pressure in the primary fluid line 5 is higher than that at the secondary IV (SIV) fluid line 7, in which no fluid flows. The higher-pressure head at the primary fluid line 5 causes the lever 120 to pivot about the fulcrum 155 such that the first end 122 of the lever 120 having the primary line sealing member thereon is tilted or otherwise rotated downstream, away from the upper surface 112 of the chamber 110. Accordingly, fluid communication between the primary fluid line 5 and the chamber 110 is established, and the primary medical fluid flows into the chamber. While the first end 122 is tilted or rotated away from the upper surface 112, the second end 124 of the lever 120 is tilted or otherwise rotated upstream towards the secondary inlet 106 until the secondary line sealing member 140 contacts and seals the secondary inlet. In this state, the secondary line sealing member 140 engages with the secondary fluid line 7 and blocks fluid communication between the secondary fluid line 7 and the chamber 110. Accordingly, the primary fluid may flow from the primary fluid line 5 to the patient 50 via the chamber and the outlet 9.

FIG. 3C illustrates an operational state of the flow control device and valve member of FIG. 3A where both the primary and secondary fluid lines 5 and 7 are engaged and fluid pressure in the secondary fluid line 7 is higher than that in the primary fluid line 5, in accordance with some embodiments of the present disclosure. When the secondary medical fluid needs to be administered, the secondary fluid line 7 may then be directly connected to the flow control device 100 to allow fluid connection between the secondary fluid line 7 and the chamber 110. Since the secondary fluid bag 10 may be positioned at a higher axial position or height than the primary fluid bag 10, the pressure head (fluid pressure) at the secondary fluid line 7 is higher than the pressure head (fluid pressure) at the primary fluid line 5. The fluid in the secondary fluid line 7 may generate a greater hydrostatic pressure on the valve member or lever 120 than the fluid in the primary fluid line 5 as a result of the primary fluid bag 10 coupled to the primary fluid line 5 being disposed at a height below the secondary fluid bag 20 coupled to the secondary fluid line 7.

In some embodiments, the higher pressure head at the secondary fluid line 7 causes the lever 120 to pivot about the fulcrum 155 such that the second end 124 of the lever 120 having the secondary line sealing member thereon is tilted or otherwise rotated downstream, away from the upper surface 112 of the chamber 110, as illustrated in FIG. 4A. Accordingly, fluid communication between the secondary fluid line 7 and the chamber 110 is established, and the secondary medical fluid flows into the chamber 110. While the second end 124 is tilted or rotated away from the upper surface 112, the first end 122 of the lever 120 is tilted or otherwise rotated upstream towards the primary inlet 104 until the primary line sealing member 130 contacts and seals the primary inlet. In this state, the primary line sealing member 130 engages with the primary fluid line 5 and blocks fluid communication between the primary fluid line 5 and the chamber 110. Hydrostatic pressure from fluid in the secondary fluid line 7 is transmitted to pivot the lever 120 so that fluid flow from the primary fluid line 5 into the chamber 110 is blocked during infusion of the secondary medical fluid. Accordingly, only fluid from the secondary fluid line 7 may flow into the chamber 114 via the secondary inlet 106. The fluid from the secondary fluid line 7 may thus be delivered to the patient 50 through the outlet 108 and outlet fluid line 9.

Accordingly, backflow of fluid from the secondary fluid line 7 into the primary fluid line 5 is prevented. Similarly, under-infusion of the secondary drug—which commonly occurs as a result of the secondary medical fluid flowing into the primary fluid line 5 from the chamber 110—may be prevented. Preventing or restricting backflow of the fluid is advantageous in that it restricts undesirable particulate matter (for example, contained in the medical fluid dispensed from the secondary fluid line 7) from flowing backwards into the primary fluid line 5 from the chamber 110 (and secondary fluid line 7), which would otherwise prevent the patient 50 from receiving the proper medical fluid (drug) dosage concentration or from timely delivery of the drug.

Referring back to FIG. 3C, the flow of medical fluid from the secondary fluid line 7 into the chamber 110 will continue until the time when the medical fluid in the secondary bag 20 is depleted. In some instances, a small quantity of the secondary medical fluid (may remain trapped in the secondary fluid line 7. This small quantity of medical fluid may be infused slowly into the chamber along with the primary medical fluids, for example, when the fluid pressures in the primary and secondary fluid lines 5 and 7 are equal, as illustrated in FIG. 3D.

FIG. 3D illustrates an operational state of the flow control device and valve member of FIG. 3A when the secondary fluid line 7 has drained to a point where fluid pressure in the primary fluid line 5 equals that in the secondary fluid line 7, in accordance with some embodiments of the present disclosure. In operation, when subject to a primary fluid pressure that equals that of a secondary fluid pressure (i.e., a pressure applied by the fluid flowing from the primary IV fluid line 5 into the primary inlet 104 that equals pressure applied by fluid flowing from the secondary IV fluid line 7 into the secondary inlet 106), the secondary medical fluid may continue to flow into the chamber 110. In particular, due to the structure of the lever 120 having the transition step 160 and the fulcrum 155 positioned on the primary portion 123 of the lever 120, which is positioned at an elevated axial position relative to the secondary portion 125, the secondary line sealing member 140 will be spaced apart from the upper surface 112 of the housing, thereby allowing the secondary medical fluid to continue to flow while primary medical fluid is blocked from entering by the elevated primary seal 130. Accordingly, when fluid pressure in the primary and secondary IV fluid lines 5 and 7 is equal, only the secondary medical fluid may be dispensed to the patient.

Once the secondary medical fluid has been depleted or near the end of the secondary infusion—due to the lack of hydrostatic pressure in the secondary fluid line 7—the lever 120 may pivot about the fulcrum 155 to cause the primary line sealing member 130 to be disengaged from the primary fluid line 5. Accordingly, fluid communication between the primary fluid line 5 and the chamber 110 may be re-established, and the primary medical fluid may flow into the chamber 110. Since the secondary fluid line 7 closes only when the pressure in the primary fluid line 5 is higher than the in the secondary fluid line 7, the secondary medical fluid will flow up until that time, thereby advantageously eliminating the dead volume in the secondary fluid line 7.

FIGS. 4A and 4B illustrate a flow control device, in accordance with some embodiments of the present disclosure. Although the flow control device 100 has been described herein with respect to the configuration illustrated in FIG. 4A, the various embodiments of the present disclosure are not limited to this configuration. In some embodiments, the housing 102 may have a shape as illustrated in FIG. 4B. In these embodiments, the structure and function of all other components of the flow control device 100 as previously described may remain the same. The housing 102 of the embodiments illustrated in FIG. 4B may provide the advantage of a smaller footprint or size potentially more suitable to utilize in the IV set 1.

In accordance with some embodiments of the present disclosure, the flow control device 100 may include a spring or other elastic body for pre-loading the lever 120. For example, the flow control device 100 may include a compression spring disposed between the secondary line sealing member 140 and the housing 102 to ensure that a pre-load or positive force is continually applied to the secondary portion 125 of the lever 120.

In some embodiments, the lever 120 may be a lever having a single arm. For example, the lever 120 may be designed without the transition step 160. In these embodiments, the single arm lever may be configured, assembled, or otherwise formed to selectively open and close the primary inlet 104 based on the fluid level inside the chamber 110. When the drug flowing into the chamber 110 from the primary inlet 104 or the secondary inlet 106 raises the fluid level in the chamber above the base of the single arm lever, the single arm lever may start to float upwards or upstream due to buoyancy force of the fluid in the chamber 110 acting on the base of the single arm lever. Accordingly, the primary sealing line member 130 may contact and close the primary inlet 104 so that only secondary fluid may flow into the chamber 110.

In one or more embodiments of the disclosure, a flow control device comprises a housing including a primary inlet, a secondary inlet, and an outlet disposed downstream of the primary and secondary inlets; a chamber defined by an inner circumferential surface of the housing, the chamber fluidly connecting the primary and secondary inlets with the outlet; and a valve member mounted in the chamber to pivot toward and block the primary inlet by fluid pressure in the secondary inlet when fluid pressure into the secondary inlet is higher than fluid pressure into the primary inlet.

In aspects of the disclosure, the chamber comprises an upper surface fluidly communicated with the primary and secondary inlets and a lower surface fluidly communicated with the outlet; and the valve member is pivotally mounted on the upper surface of the chamber. In aspects of the disclosure, the valve member comprises a lever having a first end and a second end; and a fulcrum of the lever is disposed between the first and second ends of the lever. In aspects of the disclosure, the first and second ends of the lever are positioned axially offset from each other; and the lever comprises a step having a height corresponding to the axial offset of the first and second ends.

In aspects of the disclosure, the lever comprises a primary portion and a secondary portion; the primary portion extends from the first end of the lever to the step; and the secondary portion extends from the step to the second end of the lever. In aspects of the disclosure, the fulcrum is positioned on the primary portion. In aspects of the disclosure, the lever further comprises: a primary line sealing member disposed on the primary portion at a position corresponding to the primary inlet; and a secondary line sealing member disposed on the secondary portion at a position corresponding to the secondary inlet. In aspects of the disclosure, a distance between the primary line sealing member and the fulcrum is less than a distance between the secondary line sealing member and the fulcrum. In aspects of the disclosure, in a non-actuated state of the valve member: the primary line sealing member contacts the upper surface of the chamber; and the secondary line sealing member is axially spaced apart from the upper surface of the chamber.

In one or more embodiments of the disclosure, a flow control device comprisesa housing having an inner circumferential surface defining a chamber, and including a primary inlet configured to receive a primary fluid line, a secondary inlet configured to receive a secondary fluid line, and an outlet disposed downstream of the primary and secondary inlets; and a valve member mounted on the inner circumferential surface. The valve member comprises a lever having first and second ends; a fulcrum on which the lever is supported and pivoted; a primary line sealing member disposed at the first end at a position corresponding to the primary inlet; and a secondary line sealing member disposed at the second end at a position corresponding to the secondary inlet.

In aspects of the disclosure, a distance between the primary line sealing member and the fulcrum is less than a distance between the secondary line sealing member and the fulcrum. In aspects of the disclosure, the first and second ends of the lever are positioned axially offset from each other; and the lever comprises a step having a height corresponding to the axial offset of the first and second ends. In aspects of the disclosure, the lever comprises a primary portion and a secondary portion; the primary portion extends from the first end of the lever to the step; and the secondary portion extends from the step to the second end of the lever. In aspects of the disclosure, the fulcrum is positioned on the primary portion. In aspects of the disclosure, in a non-actuated state of the valve member, the primary portion of the lever is disposed upstream of the secondary portion of the lever. In aspects of the disclosure, in a non-actuated state of the valve member: the primary line sealing member contacts an upper surface of the chamber; and the secondary line sealing member is axially spaced apart from the upper surface of the chamber.

In aspects of the disclosure, the primary fluid line is coupled to a primary fluid container, and the secondary fluid line is coupled to a secondary fluid container, the primary fluid container disposed at a height below the secondary fluid container; and fluid in the secondary fluid line generates a greater hydrostatic pressure on the valve member than the fluid in the primary fluid line as a result of the primary fluid container being disposed at the height below the secondary fluid container. In aspects of the disclosure, the primary fluid container comprises a primary intravenous (IV) fluid bag containing a primary medical fluid and the secondary fluid container comprises a secondary IV fluid bag containing a secondary medical fluid different from the primary medical fluid. In aspects of the disclosure, an air vent is disposed on an upper surface of the housing, the air vent fluidly communicated with the chamber for venting out air that is trapped in the fluid entering the chamber through the secondary fluid line. In aspects of the disclosure, the air vent comprises a hydrophilic membrane that allows air to vent though the air vent, and prevents liquid from passing therethrough.

Accordingly, the various embodiments of the present disclosure are advantageous in providing a flow control device capable of preventing under-infusion of the secondary drug by blocking the secondary drug from flowing backwards into the primary IV fluid line, as discussed previously. The flow control device of the various embodiments described herein is further advantageous as it minimizes the number of separate components of an IV set by replacing a check valve and a y-connector with the single flow control device. As a result, cost of the IV set may be reduced. Additionally, the various embodiments of the present disclosure are advantageous in reducing workflow steps for the clinician/nurses since no manual operation is necessary for flow regulation as the flow pressure of the secondary drug or fluid is used to regulate flow of the primary drug or fluid, and no priming is necessary for the secondary fluid line.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A gravitational flow control device, comprising:
   a housing including a primary inlet and a secondary inlet each disposed on an upper surface of the housing, and an outlet disposed on a lower surface of the housing gravitationally downstream of the primary and secondary inlets;
   a chamber defined by an inner circumferential surface of the housing, the chamber fluidly connecting the primary and secondary inlets with the outlet;
   a valve member mounted in the chamber to pivot toward and block the primary inlet by fluid pressure in the secondary inlet when fluid pressure into the secondary inlet is higher than fluid pressure into the primary inlet, the valve member comprising:
      a lever having a first end and a second end positioned axially offset form each other;
      a step having a height corresponding to the axial offset of the first and second ends;
      a primary portion extending from the first end to the step; and
      a secondary portion extending from the step to the second end; and
   a fulcrum disposed between the upper surface of the housing and the primary portion, the fulcrum positioned between and separate from the first end and the step.

2. The gravitational flow control device of claim 1, wherein the valve member is pivotally mounted on the upper surface of the chamber and configured to pivot in response to higher fluid pressure from gravitational fluid flow through one of the primary inlet and the secondary inlet.

3. The gravitational flow control device of claim 1, wherein the lever further comprises:
   a primary line sealing member disposed on the primary portion at a position corresponding to the primary inlet; and
   a secondary line sealing member disposed on the secondary portion at a position corresponding to the secondary inlet.

4. The gravitational flow control device of claim 3, wherein a distance between the primary line sealing member and the fulcrum is less than a distance between the secondary line sealing member and the fulcrum.

5. The gravitational flow control device of claim 3, wherein in a non-actuated state of the valve member:
   the primary line sealing member contacts the upper surface of the chamber; and
   the secondary line sealing member is axially spaced apart from the upper surface of the chamber.

6. The gravitational flow control device of claim 1, wherein the housing is a cylindrical housing comprising a circular outer wall between a flat upper surface and a flat lower surface.

7. The gravitational flow control device of claim 1, wherein the housing is an octagonal housing with the upper surface comprising a flat top portion between two angled portions, wherein the primary inlet and the secondary inlet are disposed on the two angled portions, respectively.

8. A gravitational flow control device, comprising:
   a circular housing having an inner circumferential surface defining a circular chamber, and including a primary inlet disposed on an upper surface of the housing and configured to receive a primary fluid line, a secondary inlet disposed on the upper surface of the housing and configured to receive a secondary fluid line, and an outlet disposed on a lower surface of the housing gravitationally downstream of the primary and secondary inlets; and a valve member mounted on the upper surface and comprising:

a lever comprising a primary portion having a first end and a secondary portion having a second end, wherein the first and second ends of the lever are positioned axially offset from each other and the lever comprises a step having a height corresponding to the axial offset of the first and second ends;

a fulcrum on which the lever is supported and pivoted, the fulcrum disposed between the upper surface of the housing and the lever, the fulcrum positioned between and separate from the first end and an opposing end of the primary portion;

a primary line sealing member disposed at the first end at a position corresponding to the primary inlet; and    a secondary line sealing member disposed at the second end at a position corresponding to the secondary inlet.

9. The gravitational flow control device of claim 8, wherein a distance between the primary line sealing member and the fulcrum is less than a distance between the secondary line sealing member and the fulcrum.

10. The gravitational flow control device of claim 8, wherein:

the lever comprises a primary portion and a secondary portion;

the primary portion extends from the first end of the lever to the step; and    the secondary portion extends from the step to the second end of the lever.

11. The gravitational flow control device of claim 10, wherein the fulcrum is positioned on the primary portion.

12. The gravitational flow control device of claim 10, wherein in a non-actuated state of the valve member, the primary portion of the lever is disposed upstream of the secondary portion of the lever.

13. The gravitational flow control device of claim 8, wherein in a non-actuated state of the valve member:

the primary line sealing member contacts an upper surface of the chamber; and    the secondary line sealing member is axially spaced apart from the upper surface of the chamber.

14. The gravitational flow control device of claim 8, wherein:

the primary fluid line is coupled to a primary fluid container, and the secondary fluid line is coupled to a secondary fluid container, the primary fluid container disposed at a height below the secondary fluid container; and    fluid in the secondary fluid line generates a greater hydrostatic pressure on the valve member than the fluid in the primary fluid line as a result of the primary fluid container being disposed at the height below the secondary fluid container.

15. The gravitational flow control device of claim 14, wherein the primary fluid container comprises a primary intravenous (IV) fluid bag containing a primary medical fluid and the secondary fluid container comprises a secondary IV fluid bag containing a secondary medical fluid different from the primary medical fluid.

16. The gravitational flow control device of claim 8, further comprising an air vent disposed on an upper surface of the housing, the air vent fluidly communicated with the chamber for venting out air that is trapped in the fluid entering the chamber through the secondary fluid line.

17. The gravitational flow control device of claim 16, wherein the air vent comprises a hydrophilic membrane that allows air to vent though the air vent, and prevents liquid from passing therethrough.

\* \* \* \* \*